United States Patent
Sakurai et al.

(10) Patent No.: US 7,879,903 B2
(45) Date of Patent: Feb. 1, 2011

(54) OPTICALLY ACTIVE 3-AMINOPYRROLIDINE SALT, PROCESS FOR PRODUCTION THEREOF, AND METHOD FOR OPTICAL RESOLUTION OF 3-AMINOPYRROLIDINE

(75) Inventors: Rumiko Sakurai, Fukushima (JP); Atsushi Yuzawa, Ibaraki (JP); Kenichi Sakai, Aichi (JP)

(73) Assignee: Toray Fine Chemicals Co., Ltd. (JP)

( * ) Notice: Subject to any disclaimer, the term of this patent is extended or adjusted under 35 U.S.C. 154(b) by 0 days.

(21) Appl. No.: 12/810,660

(22) PCT Filed: Dec. 22, 2008

(86) PCT No.: PCT/JP2008/073271

§ 371 (c)(1), (2), (4) Date: Jun. 25, 2010

(87) PCT Pub. No.: WO2009/084493

PCT Pub. Date: Jul. 9, 2009

(65) Prior Publication Data

US 2010/0267966 A1    Oct. 21, 2010

(30) Foreign Application Priority Data

Dec. 27, 2007    (JP) .............................. 2007-336088

(51) Int. Cl.
*C07D 207/00*    (2006.01)
*A01N 43/36*    (2006.01)

(52) U.S. Cl. ..................................... 514/426; 548/557

(58) Field of Classification Search ........................ None
See application file for complete search history.

(56) References Cited

FOREIGN PATENT DOCUMENTS

| | | |
|---|---|---|
| JP | 01-294683 | 11/1989 |
| JP | 2-218664 A | 8/1990 |
| JP | 11-506726 | 6/1999 |
| JP | 2001-072644 A | 3/2001 |
| JP | 2001-294582 A | 10/2001 |
| JP | 2004-123596 A | 4/2004 |
| JP | 2004-143170 A | 5/2004 |
| JP | 2006-008518 A | 1/2006 |
| JP | 2007-116916 A | 5/2007 |
| WO | 2006/126498 A1 | 11/2006 |

OTHER PUBLICATIONS

Sakurai et al, caplus an 2008:903513.*
Sakurai, R. et al., "Practical Resolution of 3-aminopyrrolidine via Diastereomeric Salt Formation with (S)-2-methoxy-2-phenylacetic Acid," *Tetrahedron Asymmetry*, 2008, vol. 19, pp. 1622-1625.
Marchand, P. et al., "Diastereomeric Resolution Rationalized by Phase Diagrams under the Actual Conditions of the Experimental Process," *Tetrahedron Asymmetry*, 2004, vol. 15, pp. 2455-2465.

* cited by examiner

*Primary Examiner*—Yong Chu
*Assistant Examiner*—Sun Jae Y Loewe
(74) *Attorney, Agent, or Firm*—DLA Piper LLP (US)

(57) ABSTRACT

An optically active 3-aminopyrrolidine (3AP) salt has a high optical purity which is useful as an intermediate in an industrial production method of an optically active 3AP, an efficient method for producing it, and an efficient industrial method for optical resolution of 3AP. Optical resolution of 3AP is efficiently carried out by reacting racemic 3AP with optically active 2-methoxyphenylacetic acid in the presence of a mineral acid such as hydrochloric acid in an aqueous solvent, followed by separation of the resulting diastereomer salt constituted by 1 mole of optically active 3AP and 2 moles of optically active 2-methoxyphenylacetic acid.

19 Claims, No Drawings

OPTICALLY ACTIVE 3-AMINOPYRROLIDINE SALT, PROCESS FOR PRODUCTION THEREOF, AND METHOD FOR OPTICAL RESOLUTION OF 3-AMINOPYRROLIDINE

RELATED APPLICATIONS

This is a §371 of International Application No. PCT/JP2008/073271, with an international filing date of Dec. 22, 2008 (WO 2009/084493 A1, published Jul. 9, 2009), which is based on Japanese Patent Application No. 2007-336088, filed Dec. 27, 2007, the subject matter of which is incorporated by reference.

TECHNICAL FIELD

This disclosure relates to an optically active 3-aminopyrrolidine salt, a method for production thereof, and a method for optical resolution of 3-aminopyrrolidine.

BACKGROUND

Optically active 3-aminopyrrolidine (hereinafter also referred to as "3AP") is a compound useful as a raw material for pharmaceuticals, pesticides and the like. As a method for production of an optically active 3AP, production via a N-substituted derivative such as a N-benzyl compound is known.

For example, (1) a method wherein ketone in 1-benzylpyrrolidin-3-one is converted to an amine in the presence of an optically active 1-phenylethylamine using transaminase (JP 2007-1116916 A; Yield: 71%, 88% ee):

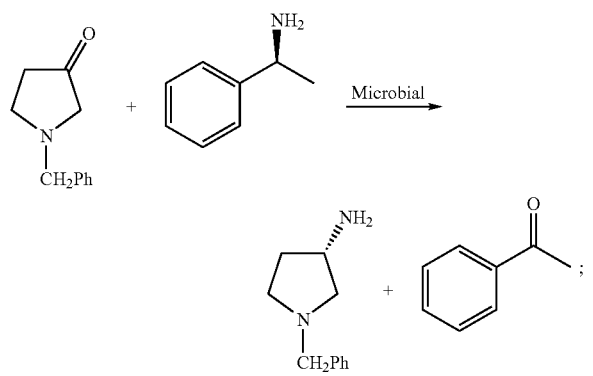

(2) a method wherein 1-benzylpyrrolidin-3-one is induced to an amine in the presence of an optically active 1-phenylethylamine using an enzyme (WO 2006-126498 A1; Yield: 75%, 79% ee):

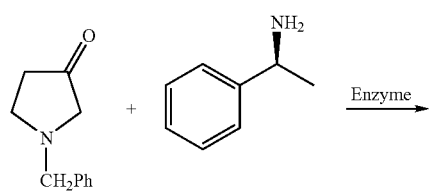

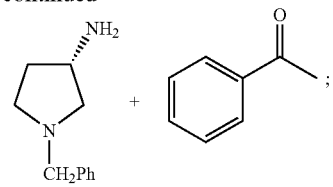

(3) a method wherein 4-hydroxyproline is decarboxylated and converted to an azide via N-tert-butoxycarbonylation and O-mesylation, which azide is reduced by hydrogenation to obtain a N-Boc compound (JP 2006-008518 A; Yield and optical purity are unknown):

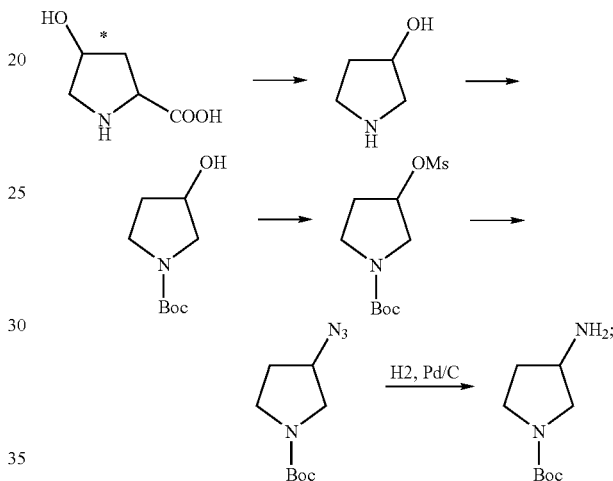

and (4) optical resolution of racemic 1-benzyl-3-aminopyrrolidine by L-tartaric acid (TA)(JP 2-218664 A):

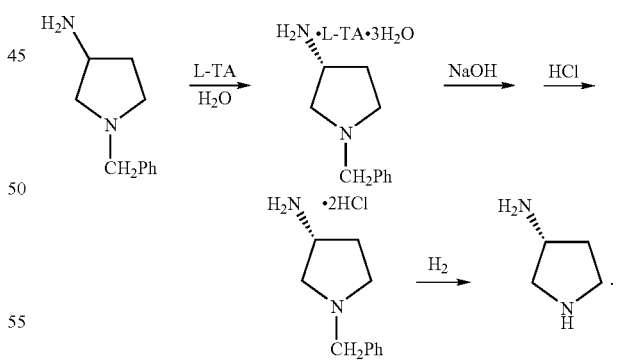

A method by direct resolution of 3AP by L-tartaric acid is also known, but this is industrially incomplete because of, for example, instability of crystallization, wherein salt crystals containing the (S) compound first precipitate, followed by precipitation of the salt containing the (RS) compound and then the salt containing the (R) compound.

Thus, although several methods for producing 3 AP are known, all of these have drawbacks such as low optical purities of the obtained desired products. Further, in these production methods, to obtain 3AP, a step for removing a N-substituent is required, which is complicated.

Thus, at present, by conventional technology, optically active 3AP cannot be produced conveniently at a high yield. Hence, creation of an efficient industrial production method has been demanded. It could thus be helpful to provide: an optically active 3AP salt having a high optical purity which is useful as an intermediate in an industrial production method of an optically active 3AP; an efficient method for producing it; and an efficient industrial method for optical resolution of 3AP.

SUMMARY

We discovered that optical resolution of 3AP can be efficiently carried out by reacting racemic 3AP with optically active 2-methoxyphenylacetic acid (hereinafter also referred to as "MPAA") in the presence of a mineral acid such as hydrochloric acid in an aqueous solvent, followed by separation of the resulting diastereomer salt constituted of 1 mole of optically active 3AP and 2 moles of optically active MPAA.

That is, we provide a salt composed of one molecule of optically active 3-aminopyrrolidine and 2 molecules of optically active 2-methoxyphenylacetic acid, represented by the Formula [I] below:

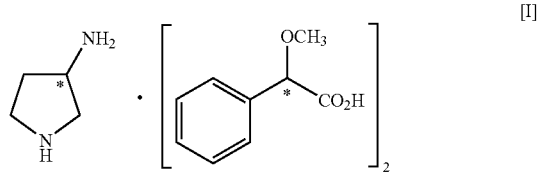

(wherein * identifies a carbon atom having an asymmetric center, and in cases where the 2-methoxyphenylacetic acid has an (S) configuration, the 3-aminopyrrolidine has an (R) configuration, while in cases where the 2-methoxyphenylacetic acid has an (R) configuration, the 3-aminopyrrolidine has an (S) configuration.

Further, we provide a method for producing the above-described salt comprising reacting racemic 3-aminopyrrolidine with optically active 2-methoxyphenylacetic acid and separating the salt produced thereby. We also provide a method of optical resolution of 3-aminopyrrolidine comprising reacting racemic 3-aminopyrrolidine with optically active 2-methoxyphenylacetic acid and separating the salt produced thereby.

Thus, an optically active 3AP salt having a high optical purity which is an intermediate of an optically active 3AP can be produced at a commercial scale, simply and at a high yield.

DETAILED DESCRIPTION

As described above, the optically active 3AP salt has the chemical structure represented by the above Formula [I]. In Formula [I], * represents a carbon atom having an asymmetric center. In the case where the optically active MPAA has an (S) configuration, the configuration of the optically active 3AP is (R), while in the case where the optically active MPAA has an (R) configuration, the configuration of the optically active 3AP is (S).

The optically active 3AP salt represented by the above Formula [I] can be produced by reacting racemic 3AP with optically active MPAA and separating the salt produced thereby.

The above-described reaction can be carried out using water as the reaction solvent. This is one of the advantageous characteristics of our method. Other than water, an organic solvent which can be blended with water at an arbitrary ratio, such as methanol or ethanol; or a mixture of water and the organic solvent may be used. However, water is most preferred in view of simplicity of purification of the product and cost.

The reaction temperature is not limited as long as it is a temperature at which crystals of the salt represented by the above Formula [I] precipitate, and it is usually 1° C. to 30° C., preferably 15° C. to 25° C. To completely dissolve the starting materials, the initial temperature of the reaction is usually set to a high temperature of about 50° C. to 70° C., which is slowly cooled down to a final temperature of, as described above, usually 1° C. to 30° C., preferably 15° C. to 25° C. The reaction time is not limited, and at a temperature within the above-described range, that is, usually 1° C. to 30° C., preferably 15° C. to 25° C., it is about 15 minutes to 4 hours, preferably 30 minutes to 2 hours.

Racemic 3AP, which is one of the starting materials, may be either in the form of a free base (that is, in the form of a compound which is not forming a salt) or in the form of a dimineral acid salt such as an acid addition salt formed with a mineral acid such as hydrochloric acid. In cases where the racemic 3AP used as a starting material is in the form of a dimineral acid salt, it is difficult to be dissolved completely into the solvent, so that it is preferably converted to the free base by inclusion of an inorganic base such as NaOH in the reaction solution when the reaction is initiated. The amount of the inorganic base to be used in this case is preferably the stoichiometric amount required for neutralization of the acid in the acid addition salt of 3AP, or a vicinity thereof (0.8 to 1.2 times as much as the stoichiometric amount).

We discovered that, by setting the reaction ratio of the optically active MPAA with respect to the racemic 3AP as a starting material lower than the stoichiometric amount, it is possible to keep a high optical purity of the salt of Formula [I], which is the desired product, and increase the yield. That is, we discovered that, by the reaction in the proportion of 1 mole of racemic 3AP as a starting material to 0.5 to 1.5 moles, preferably 0.8 to 1.2 moles, most preferably 1.0 mole of optically active MPAA, high optical purity and high yield can be satisfied at the same time. Further, we discovered that, by the reaction in the presence of a mineral acid, optical purity and yield become high. In particular, by satisfying both conditions, that is, by the reaction in the proportion of 1 mole of racemic 3AP as a starting material to react with 0.5 to 1.5 moles, preferably 0.8 to 1.2 moles, most preferably 1.0 mole of optically active MPAA in the presence of a mineral acid, an especially excellent optical purity and yield can be satisfied at the same time. In such a case, the mineral acid is preferably a strong acid such as hydrochloric acid or sulfuric acid, especially preferably hydrochloric acid. In terms of the amount of the mineral acid to be used, the sum of the product of the valency and the number of moles of the mineral acid and the number of moles of the optically active 2-methoxyphenylacetic acid is preferably 1.6 to 2.4, more preferably 1.8 to 2.2, most preferably 2.0 with respect to 1 mole of the racemic 3AP. That is, in cases where the mineral acid is a monovalent mineral acid such as hydrochloric acid, the sum of the total number of moles of the mineral acid and the optically active MPAA with respect to 1 mole of the 3AP is preferably 1.6 to 2.4 moles, more preferably 1.8 to 2.2 moles, most preferably 2.0 moles, and in cases where the mineral acid is a divalent acid such as sulfuric acid, the number of moles is a half of that in the case of hydrochloric acid.

In cases of the reaction in the presence of a mineral acid, which is preferred, the mineral acid may be included in the reaction system from the beginning, but it is preferably slowly added to the reaction system by dropwise addition or the like while being reacted, in view of satisfaction of high optical purity and high yield. In particular, in cases where a dimineral acid salt of 3AP is used as a starting material, it is preferably preliminarily converted to the free base with NaOH or the like as described above so that the mineral acid is preferably slowly added after the conversion.

By the above method, crystals of the salt of Formula [I], which is the desired product, precipitate in the reaction solution. The precipitated crystals can be recovered by a conventional method such as centrifugation or filtration.

The obtained salt can be easily made to have an optical purity of not less than 99% by recrystallization from water. Recrystallization from water can be carried out by once converting the salt to the free base by an inorganic base such as NaOH and slowly adding a mineral acid thereto by dropwise addition or the like, followed by slowly cooling the resulting mixture. Recrystallization can be carried out in the same manner as in the preferred mode in the case of usage of a dimineral acid salt as 3AP in the above-described method for production of the salt, except that MPAA is not added.

Further, optically active 3AP can be easily separated and purified from the salt by conversion to the free base by alkali, extraction operation and/or distillation operation.

precipitation of salt crystals, and pH of the slurry after the dropwise addition of all the hydrochloric acid was 5. Thereafter, the slurry liquid was slowly cooled (cooling time: 3 hours), and when the temperature reached 20° C., the reaction mixture was stirred for 1 hour, followed by solid-liquid separation by centrifugation. The salt crystals were washed with water and subjected to centrifugation to obtain 61.8 kg of wet crystals (dry weight: 53.8 kg) of the (R)-3AP.2((S)-MPAA) salt (yield with respect to the racemic compound: 43.7%; optical purity of 3AP in the salt: 98.3%).

Examples 2 to 8

By basically the same method as in Example 1, the salt was produced by reacting racemic 3AP dihydrochloric acid as a starting material with (S)-MPAA. The amounts of the starting materials, the reaction ratios, the type of the solvent, and the amount of the solvent (how many times as much as the amount of 3AP) are shown in Table 1 below. The yield of the salt, the optical purity of (R)-3AP in the salt and the resolution efficiency (%) are shown in Table 1. The resolution efficiency (%) is a value calculated by:

resolution efficiency (%)=yield (%)×2× optical purity (%)/$10^2$.

Table 1 also shows the results of the above Example 1.

TABLE 1

| Example | 3AP•2HCl | S-MPAA | MPAA/3AP molar ratio | Hydrochloric acid/3AP molar ratio | Solvent type | Amount of solvent vs RS-3AP | Yield of salt vs RS-3AP | Optical purity of (R)-3AP component in salt | Resolution efficiency |
|---|---|---|---|---|---|---|---|---|---|
| 1 | 50 kg | 47.8 kg | 1.0 | 1.0 | Water | ×8 | 43.7% | 98.3% | 85.9% |
| 2 | 2 g | 2.09 g | 1.0 | None | Water | ×8 | 11.0% | 99.5% | 21.9% |
| 3 | 1 g | 1.25 g | 0.8 | 1.2 | Water | ×10 | 33.1% | 94.1% | 62.3% |
| 4 | 2 g | 2.09 g | 1.0 | 1.0 | Water | ×10 | 38.8% | 96.8% | 75.1% |
| 5 | 10 g | 9.4 g | 1.0 | 1.0 | Water | ×8 | 44.6% | 93.0% | 83.0% |
| 6 | 10 g | 11.3 g | 1.2 | 0.8 | Water | ×8 | 48.0% | 92.6% | 88.9% |
| 7 | 10 g | 141 g | 1.5 | 0.5 | Water | ×8 | 51.6% | 85.2% | 87.9% |
| 8 | 205 g | 240 g | 1.1 | 1.1 | Water | ×9 | 44.0% | 98.0% | 86.2% |

Since optically active 3AP can be easily separated from the above-described salt by a conventional method, the method for production of the salt described above can be regarded as a method of optical resolution of racemic 3AP. That is, we also provide a method of optical resolution of 3AP comprising reacting racemic 3AP with optically active MPAA and separating the salt produced thereby. Detailed and preferred conditions of this method are the same as those of the production method of the above-described salt.

Our compounds and methods will now be described more concretely by way of Examples. However, this disclosure is not restricted to the following Examples.

EXAMPLES

Example 1

In a 500 L reactor, 50 kg of racemic 3AP dihydrochloric acid salt and 203 L of water were placed, followed by feeding 85 kg of 30% NaOH thereto and stirring the resulting mixture. Further, 47.8 kg of (S)-MPAA was fed thereto and the resulting mixture was dissolved by heating (60° C.). After confirming the dissolution, 36.3 kg of 35% hydrochloric acid was slowly added dropwise to the solution. This resulted in slow As shown in Table 1, it can be seen that optical resolution of racemic 3AP is possible at a high optical purity. Since, in Example 2, hydrochloric acid was not added dropwise, the optical purity of the (R)-3AP in the resulting salt was extremely high, but the yield of the salt was low, and therefore the resolution efficiency was also low. In contrast, it can be seen that, in other Examples wherein hydrochloric acid was added dropwise, the optical purity was rather low, but the yield was largely improved while maintaining a practically sufficiently high optical purity so that the resolution efficiency was largely improved. As described concretely in Examples 9 and 10 below, the optical purity can be made extremely high by recrystallization treatment of the salt.

Example 9

Purification of Salt

By the method described in Example 1, salt crystals (crude salt crystals) were produced, and the total amount of the obtained salt crystals (wet crystals), 261 kg of water, and 34.3 kg of 30% NaOH were fed to a 500 L reactor, followed by heating the resulting mixture with stirring to once convert the salt to the free base (60° C.). To the resultant, 26.8 kg of 35% hydrochloric acid was slowly added dropwise. This resulted in slow precipitation of salt crystals. The slurry liquid was slowly cooled, and when the temperature reached 20° C., the reaction mixture was stirred for 1 hour, followed by solid-liquid separation by centrifugation. The salt crystals were washed with water and centrifuged to obtain 47.1 kg of wet salt crystals (dry weight: 43.6 kg) (recrystallization yield: 81%, optical purity of 3AP in the salt: 99.6%).

The analytical results of the salt recrystallized in Example 1 are as follows:

Analytical results: (R)-3AP.2((S)-MPAA) salt
Mw: 418.45
Outer appearance: powder having a white to light brown color
Melting point: 222 to 223° C.
Specific rotation: +91.88° (c 0.5, water)
Optical purity: 99.6% ((R)-3AP in the salt)
IR: 3446, 2997, 2931, 2875, 2823, 2208, 1639, 1572, 1495, 1450, 1400, 1338, 1198, 1099, 1072, 1030, 993, 957, 916, 783, 731, 698, 602.
NMR: $^1$H NMR (D$_2$O, 400 MHz): δ 7.27-7.20 (10H, m), 4.47 (2H, s), 3.94 (1H, tt, J=8.0, 6.0 Hz), 3.58 (1H, dd, J=13.2, 8.0 Hz), 3.37 (1H, ddd, J=12.4, 7.6, 6.8 Hz), 3.28-3.20 (2H, m), 3.19 (6H, s), 2.39-2.29 (1H, m), 2.01-1.92 (1H, m).

Example 10

By basically the same method as in Example 9, the salt obtained in the above-described Example 4 was purified by recrystallization. The employed conditions and the results are shown in Table 2 below. Table 2 also shows the conditions and the results of the above-described Example 9.

Meanings of the abbreviations in Table 3 are as follows:
TA: tartaric acid; DBTA: dibenzoyl tartaric acid; DTTA: di-p-toluoyl tartaric acid; MA: mandelic acid; AcMA: O-acetylmandelic acid; MBPA: N-(1-methylbenzyl)phthalic acid monoamide; PPC: 1-(phenylethyl)-5-oxo-3-pyrrolidinecarboxylic acid; MPAA: 2-methoxyphenylacetic acid; EtOH: ethanol; and IPA: isopropanol.

As shown in Table 3, in the cases where a known optical resolution agent other than L-dibenzoyl tartaric acid was used, salt crystals were not produced. Hence, optical resolution of racemic 3AP could not be carried out at all. In the case where L-dibenzoyl tartaric acid was used, optical resolution was possible, but the optical purity of the produced salt was lower than that of the salt produced by our method and, since this case requires blending of ethanol with water as the solvent, purification is laborious compared to the case of usage of only water.

The invention claimed is:

1. A salt comprising one molecule of optically active 3-aminopyrrolidine and 2 molecules of optically active 2-methoxyphenylacetic acid, represented by the Formula [I] below:

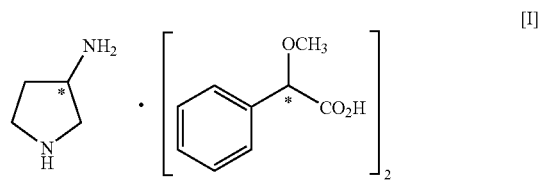

[I]

(wherein * identifies a carbon atom having an asymmetric center, and in cases where the 2-methoxyphenylacetic acid has an (S) configuration, the 3-aminopyrrolidine has an (R) configuration, while in cases where the 2-methoxyphenylacetic acid has an (R) configuration, the 3-aminopyrrolidine has an (S) configuration.

TABLE 2

| Example | Crude salt crystals | Optical purity | Solvent type | Amount of solvent vs crude salt | Recrystallization yield | Optical purity of (R)-3AP component in salt | Total yield vs RS-3AP | Total yield vs R-3AP |
|---|---|---|---|---|---|---|---|---|
| 9 | 53.8 kg | 98.3% | Water | ×4.9 wt | 81.0% | 99.6% | 35.4% | 70.8% |
| 10 | 2.0 g | 96.8% | Water | ×17.6 wt | 62.5% | >99.9% | 24.3% | 48.6% |

Comparative Examples 1 to 8

As alternatives to optically active MPAA, known optical resolution agents were used for optical resolution of racemic 3AP. The reaction conditions and the results are shown in Table 3 below.

TABLE 3

| Comparative Example | Optical resolution agent | Molar ratio of optical resolution agent vs RS-3AP | Solvent type | Amount of solvent vs RS-3AP | Yield of salt vs RS-3AP | Optical purity of (R)-3AP component in salt | Resolution efficiency |
|---|---|---|---|---|---|---|---|
| 1 | L-TA | 1.0 | MeOH/Water | ×2.1/2.7 | | Oil | |
| 2 | L-TA | 1.0 | Water | ×5 | | No crystallization | |
| 3 | L-DBTA | 1.0 | EtOH/Water | ×5/1 | 15.6% | R 76.6% | 23.9% |
| 4 | L-DTTA | 1.0 | EtOH/Water | ×5/1 | | No crystallization | |
| 5 | (S)-MA | 1.0 | EtOH/Water | ×3/1 | | No crystallization | |
| 6 | (S)-AcMA | 1.0 | EtOH/Water | ×5/5 | | No crystallization | |
| 7 | (R)-MBPA | 1.0 | IPA/Water | ×2/1 | | No crystallization | |
| 8 | (1R, 3R)-PPC | 1.0 | IPA/Water | ×2/1 | | No crystallization | |

2. The method for producing the salt according to claim 1, comprising reacting racemic 3-aminopyrrolidine with optically active 2-methoxyphenylacetic acid and separating the salt produced thereby.

3. The method according to claim 2, wherein the reaction uses water as a reaction solvent.

4. The method according to claim 2, wherein said racemic 3-aminopyrrolidine is a free base or a dimineral acid salt.

5. The method according to claim 2, carried out in the presence of a mineral acid.

6. The method according claim 2, wherein 1 mole of said racemic 3-aminopyrrolidine is reacted with 0.5 to 1.5 moles of said optically active 2-methoxyphenylacetic acid.

7. The method according to claim 6, wherein the reacting is carried out in the presence of a mineral acid, and the sum of a product of valency and a number of moles of said mineral acid and a number of moles of said optically active 2-methoxyphenylacetic acid is 1.6 to 2.4 with respect to 1 mole of said racemic 3-aminopyrrolidine.

8. A method of optical resolution of 3-aminopyrrolidine comprising reacting racemic 3-aminopyrrolidine with optically active 2-methoxyphenylacetic acid and separating the salt produced thereby.

9. The method according to claim 3, wherein said racemic 3-aminopyrrolidine is a free base or a dimineral acid salt.

10. The method according to claim 3, carried out in the presence of a mineral acid.

11. The method according to claim 4, carried out in the presence of a mineral acid.

12. The method according to claim 9, carried out in the presence of a mineral acid.

13. The method according to claim 3, wherein 1 mole of said racemic 3-aminopyrrolidine is reacted with 0.5 to 1.5 moles of said optically active 2-methoxyphenylacetic acid.

14. The method according to claim 4, wherein 1 mole of said racemic 3-aminopyrrolidine is reacted with 0.5 to 1.5 moles of said optically active 2-methoxyphenylacetic acid.

15. The method according to claim 5, wherein 1 mole of said racemic 3-aminopyrrolidine is reacted with 0.5 to 1.5 moles of said optically active 2-methoxyphenylacetic acid.

16. The method according to claim 9, wherein 1 mole of said racemic 3-aminopyrrolidine is reacted with 0.5 to 1.5 moles of said optically active 2-methoxyphenylacetic acid.

17. The method according to claim 10, wherein 1 mole of said racemic 3-aminopyrrolidine is reacted with 0.5 to 1.5 moles of said optically active 2-methoxyphenylacetic acid.

18. The method according to claim 11, wherein 1 mole of said racemic 3-aminopyrrolidine is reacted with 0.5 to 1.5 moles of said optically active 2-methoxyphenylacetic acid.

19. The method according to claim 12, wherein 1 mole of said racemic 3-aminopyrrolidine is reacted with 0.5 to 1.5 moles of said optically active 2-methoxyphenylacetic acid.

* * * * *